US005776477A

United States Patent [19]

Ryder

[11] Patent Number: 5,776,477
[45] Date of Patent: Jul. 7, 1998

[54] ORGANIC INSECT REPELLENT

[76] Inventor: Kathleen A. Ryder, 208 Chestnut St.,
Middleburg, Va. 22117

[21] Appl. No.: 676,419

[22] Filed: Jul. 8, 1996

[51] Int. Cl.$^6$ ..................................................... A01N 25/04
[52] U.S. Cl. ........................ 424/405; 424/406; 424/195.1;
424/DIG. 10; 514/919
[58] Field of Search ................................ 424/405, 406,
424/195.1, DIG. 10; 514/783, 919

[56] References Cited

U.S. PATENT DOCUMENTS

| 3,923,997 | 12/1975 | Meuly | 424/45 |
|---|---|---|---|
| 4,193,986 | 3/1980 | Cox | 424/28 |
| 4,671,960 | 6/1987 | Thielen et al. | 424/195.1 |
| 4,988,507 | 1/1991 | Wilson | 424/84 |
| 5,055,299 | 10/1991 | Dohara et al. | 424/405 |
| 5,106,622 | 4/1992 | Sherwood et al. | 424/195.1 |
| 5,165,932 | 11/1992 | Horvath | 424/195.1 |
| 5,208,029 | 5/1993 | Plummer et al. | 424/405 |
| 5,320,066 | 6/1994 | Gunter | 119/23.5 |
| 5,465,689 | 11/1995 | Winder | 119/861 |

FOREIGN PATENT DOCUMENTS

| 2447681 | 10/1980 | France . |
|---|---|---|
| 4012224 | 10/1991 | Germany . |
| 165341 | 12/1994 | Poland . |

*Primary Examiner*—Neil S. Levy
*Attorney, Agent, or Firm*—Longacre & White

[57] ABSTRACT

An environmentally safe, topical pest repellent is described. The repellent comprises a variable mixture of natural ingredients including pennyroyal herb, tansy herb, calendula, citronella, pyrethrin and aloe vera. A method is provided to produce tinctures which are combined to form a composition for application to skin of animals such as horses to repel pests such as flies, mosquitos, ticks, and other insects. The composition may be applied to animals by spraying or other suitable devices and carriers.

2 Claims, No Drawings

ORGANIC INSECT REPELLENT

BACKGROUND OF THE INVENTION a) Field of the Invention

This invention relates to a composition for the treatment of animals, and more particularly relates to a new formulation of natural ingredients for repelling pests such as flies and mosquitos from household and domestic animals.

b) Description of Related Art

Insect infestation of animals and humans has been a problem through the ages. While improvements in hygiene and sanitation have eliminated the problem for human beings in most parts of the world, household pets and domestic animals still are subject to insect infestation. While the problem is especially apparent to owners of household pets such as cats and dogs since these animals often have a great deal of contact with their owners, domestic animals also suffer from the harmful effects of these pests due to their prolonged exposure.

Both household and domestic animal owners dedicate substantial time and money each year in an effort to protect animals against pests such as insects. One of the major expenditures is in the area of fly repellents for domestic animals. A variety of products are commercially available for repelling flies including shampoos, sprays, powders and the like.

An important concern of pet owners is the hazardous character of the chemicals used in the fly repellents. Not only is the owner concerned about the effect such chemicals will have on the health of his pet, but also the effect of such chemicals on the health of the members of the community who are in contact with the animal. In view of this hazard, animal owners and handlers are in need of a new treatment for their animals that eliminates flies and other insects, and yet is not hazardous to the animal or persons coming into contact with the animal.

U.S. Pat. No. 5,102,622, which is incorporated herein by reference, provides a discussion of the various efforts to overcome the harmful effects of chemicals and to develop suitable organic repellents. However, the solutions discussed in this patent lack the necessary skin conditioning and insect repelling characteristics necessary for a suitable and efficient composition.

SUMMARY OF THE INVENTION

The present invention provides a novel composition for the treatment of animals and particularly domestic animals such as horses. The pest-repellent composition of the invention is formulated of natural ingredients which is easily formulated with commercially available materials using conventional mixing techniques in a novel manner. Also, the pest-repellent composition of the invention is relatively inexpensive.

The invention relates to a repellent composition comprising various mixtures of pennyroyal herb, tansy herb, vinegar, isopropyl alcohol, calendula, pure Ceylon citronella oil, pyrethrin and pure aloe vera juice.

The composition is produced by making two separate tinctures and mixing them together with small amounts of flower oil and an insecticide. The first tincture is made by drying 3 parts pennyroyal and 1 part tansy herb. These ingredients are mixed with isopropyl alcohol and acetic acid and agitated for a predetermined period of time, then the ingredients are strained. The second tincture, which soothes and promoted healing of skin, is made by mixing calendula (flowers) in a container having acetic acid and alcohol. The container is sealed and agitated. The calendula is strained by filter the liquid into a separate container. These first and second tinctures are then mixed together and combined with an insect repellent and an active insecticidal constituent of a flowering plant. This mixture is then stirred constantly while being poured into separate containers for use.

In the preferred embodiment, the composition of this invention is applied to animals by a spray device, but other suitable forms of administering the solution, e.g. soap, shampoo, lotion, etc., may be used.

The foregoing combination of organic ingredients and the method of producing the composition of this invention provides a non-irritating insect repellent that has skin conditioning properties and a pleasant fragrance. Other benefits and advantages of the novel repellent composition of the invention will be apparent from the following description.

DETAILED DESCRIPTION OF THE PREFERRED EMBODIMENTS

As described herein, the invention is a composition suitable for use as a topical solution for living beings and having pest repellent properties. This invention is not intended to be limited to insects but has been shown to repel a variety of creatures which prosper at the expense of a host animal.

The composition of this invention is produced by making two separate tinctures and mixing them together with small amounts of flower oil and an insecticide. The first tincture is made by drying about 3 parts pennyroyal to about 1 part tansy herb. These herbs are placed in a container and combined with about 2 parts isopropyl alcohol to about 3 parts acetic acid. The container is sealed and agitated periodically for a number of days. After the predetermined period of time, the herbs are stained by filtering the liquid into a separate container.

The second tincture, which soothes and promotes healing of the skin, is made by placing calendula (flowers) in a container having two parts acetic acid to one part alcohol. The container of the second tincture is sealed and agitated periodically for a number of days. After the predetermined period of time, the calendula is strained by filtering the liquid into a separate container.

The third step involves mixing the first and second tinctures together while adding an insect repellent (pure Ceylon citronella oil) and an active insecticidal constituent of a flowering plant (pyrethrin) to the mixture. Also added is pure aloe vera juice; a constituent that is not only soothing and healing to the skin, but reduces the astringency of the isopropyl alcohol. This mixture is then stirred constantly while being poured into containers.

The foregoing mixture is applied to the external surfaces of animals to repel flies, mosquitos, etc. while maintaining a pleasant odor and acceptable toxicity due to its organic nature.

In a particularly preferred composition and method, the constituents of the composition are as follows. These ingredients and relative amounts are set forth by way of example only and are not intended to limit the invention in any manner.

Tincture 1

1½ pounds of pennyroyal (hedeoma pulegioides)
½ pound of tansy herb (tanacetum)
3 gallons acetic acid (vinegar)
2 gallons 70% isopropyl alcohol

Tincture 2

1 pound calendula 2 gallons acetic acid (vinegar)

1 gallon 70% isopropyl alcohol

The first tincture is made by drying the pennyroyal and tansy herbs and placing them in a container. The isopropyl alcohol and acetic acid are added to the herbs. The container is then sealed and the mixture is agitated daily for three weeks. After the third week, the herbs are stained by filtering the liquid into a separate container.

The second tincture is made by placing the calendula (flowers) in a container having the acetic acid and alcohol. The container is sealed and agitated for three weeks. After the third week, the calendula is strained by filter the liquid into a separate container.

Next the first and second tinctures are mixed together adding about 6 ounces of pure Ceylon citronella oil and about 5 ounces of pyrethrin. An amount (about 8 ounces in this example) of pure aloe vera may also be added at this point. This mixture is then stirred constantly while being poured into containers.

The above description shows that the present invention provides a novel formulation for the treatment of animals and especially the treatment of domestic animals against flies. Of course, the exact amount or ratio of each ingredient may be varied within a reasonable range without departing from the spirit of this invention. The composition of the invention is easily formulated from natural ingredients which are commercially available.

Conventional mixing techniques may be employed in the formulation of the composition. It will be apparent that various modifications can be made in the particular formulation described in detail above within the scope of the invention. For example, other ingredients may be incorporated in the formulation provided they do not have a deleterious effect on the performance characteristics of the composition of the invention. It may be desirable in some applications to change the odor, color, viscosity or other aspects of the composition. In addition, the inert vehicle may be different to meet specific requirements, e.g. a powder. Therefore, the scope of the invention is to be limited only by the following claims.

I claim:

1. An organic composition for the treatment of animals against pestilent beings, said composition comprising:
   - a first amount of pennyroyal, tansy, acetic acid and isopropyl alcohol, said pennyroyal and tansy is derived by mixing pennyroyal herb and tansy herb with said acetic acid and said isopropyl alcohol in a first tincture, a ratio of pennyroyal herb to tansy herb is between 4:1 and 2:1 and said isopropyl alcohol is between 40% and 80% by weight of said acetic acid, wherein said isopropyl alcohol serves to enhance beneficial properties of said pennyroyal herb and said tansy herb;
   - a second amount of calendula, acetic acid and isopropyl alcohol, said calendula derived by mixing calendula herbs with isopropyl alcohol in a second tincture, said isopropyl alcohol is between 40% and 80% by weight of said acetic acid, said isopropyl alcohol serving to enhance beneficial properties of said calendula, wherein a ratio of calendula herb to tansy herb is about 2:1;
   - a third amount of citronella oil which is between about 2% and 7% by weight of said composition, and
   - a fourth amount of pyrethrin which is between about 1% and 6% by weight of said composition.

2. A composition according to claim 1, wherein said first amount is between 50% and 75% by weight of said composition.

* * * * *